United States Patent
Fischer et al.

(12) 
(10) Patent No.: US 6,569,122 B2
(45) Date of Patent: May 27, 2003

(54) SYRINGE APPARATUS FOR DELIVERING LIGHT ACTIVATED MATERIALS

(75) Inventors: Dan E. Fischer, Sandy, UT (US); Richard N. Rachal, Sandy, UT (US); Bruce S. McLean, Sandy, UT (US)

(73) Assignee: Ultradent Products, INC, South Jordan, UT (US)

( * ) Notice: Subject to any disclaimer, the term of this patent is extended or adjusted under 35 U.S.C. 154(b) by 0 days.

(21) Appl. No.: 09/765,175

(22) Filed: Jan. 18, 2001

(65) Prior Publication Data

US 2002/0094506 A1 Jul. 18, 2002

(51) Int. Cl.⁷ ................................................ A61M 5/00
(52) U.S. Cl. ........................ 604/181; 604/211; 604/218
(58) Field of Search ................................ 604/181, 211, 604/218, 182, 59; 433/89, 90; 222/137, 390

(56) References Cited

U.S. PATENT DOCUMENTS

| | | | |
|---|---|---|---|
| 4,189,065 A | 2/1980 | Herold | 222/46 |
| 4,312,343 A | 1/1982 | La Veen et al. | 128/218 |
| 4,710,179 A | 12/1987 | Haber et al. | 604/211 |
| 4,941,873 A * | 7/1990 | Fischer | |
| 5,318,544 A | 6/1994 | Drypen et al. | 604/210 |
| 5,387,103 A | 2/1995 | Fischer | 433/89 |
| 5,464,348 A | 11/1995 | Fischer et al. | 433/26 |
| 5,603,701 A * | 2/1997 | Fischer | |
| 5,618,273 A | 4/1997 | Fischer | 604/211 |
| 5,681,317 A * | 10/1997 | Caldarise | |
| 6,110,151 A * | 8/2000 | Spool et al. | |
| 2001/0029354 A1 * | 10/2001 | Rolle et al. | |
| 2002/0113088 A1 * | 8/2002 | Pierson et al. | |

OTHER PUBLICATIONS

US 2001/0029354 A1; Oct. 11, 2001; Rolle et al.*
US 2002/0113088 A1; Aug. 22, 2002; Pierson et al.*

* cited by examiner

Primary Examiner—Steven O. Douglas
Assistant Examiner—Khoa Huynh
(74) Attorney, Agent, or Firm—Workman, Nydegger & Seeley (57) ABSTRACT

A syringe is provided that has an opaque barrel and a light colored outlet portion. The opaque barrel protects dental composite material or other light-activating material contained in the barrel from premature exposure to light. The light colored outlet portion has a color that is similar to that of the dental composite material. The outlet portion may be tubular and extend coaxially within the barrel beyond the barrel. The outlet portion may include a divider that divides the material into at least two separate portions.

11 Claims, 7 Drawing Sheets

SYRINGE APPARATUS FOR DELIVERING LIGHT ACTIVATED MATERIALS

BACKGROUND OF THE INVENTION

1. The Field of the Invention

This invention relates to syringe systems that are used for storing and dispensing materials therefrom. More particularly, the present invention relates to a dental syringe system that provides for controllable doses of a solid but pliable light activated dental composite and that prevents substantial discoloration of the composite material when the composite material is being applied to the dental construction.

2. The Prior State of the Art

The prior art addresses syringes which are constructed to progressively extrude solid, yet pliable materials such as composite materials that are used in clinical dental procedures. The extrudent in dental procedures may be a light-cured composite material. Once the material is extruded from the syringe, it must be directed to the site where the material is to be applied. The material may be extruded directly onto an application site by contacting the site directly with the tip of the syringe. However, such direct placement may cause contamination of a large portion of the material when the application site is not sterile. Thus, direct application is not the best means of application of the extruded material where concern for cross contamination exists and adequate safeguards are not present.

Figure 1A:
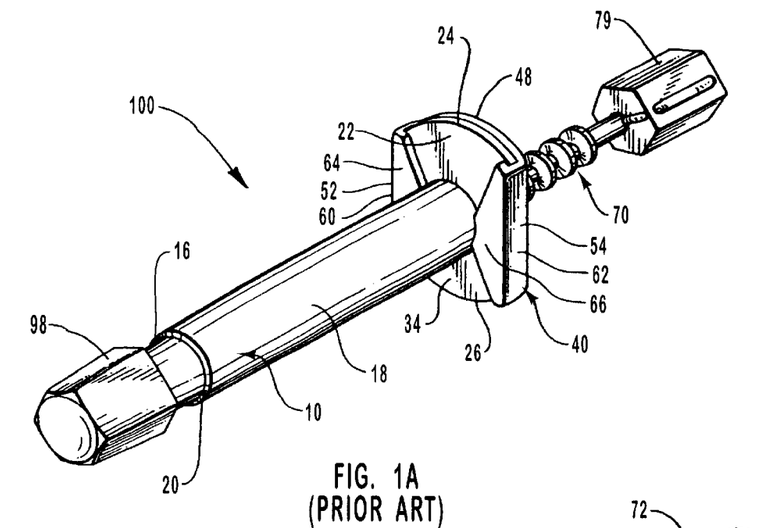
FIG. 1A is a perspective view of an assembled prior art device.
Figure 1B:
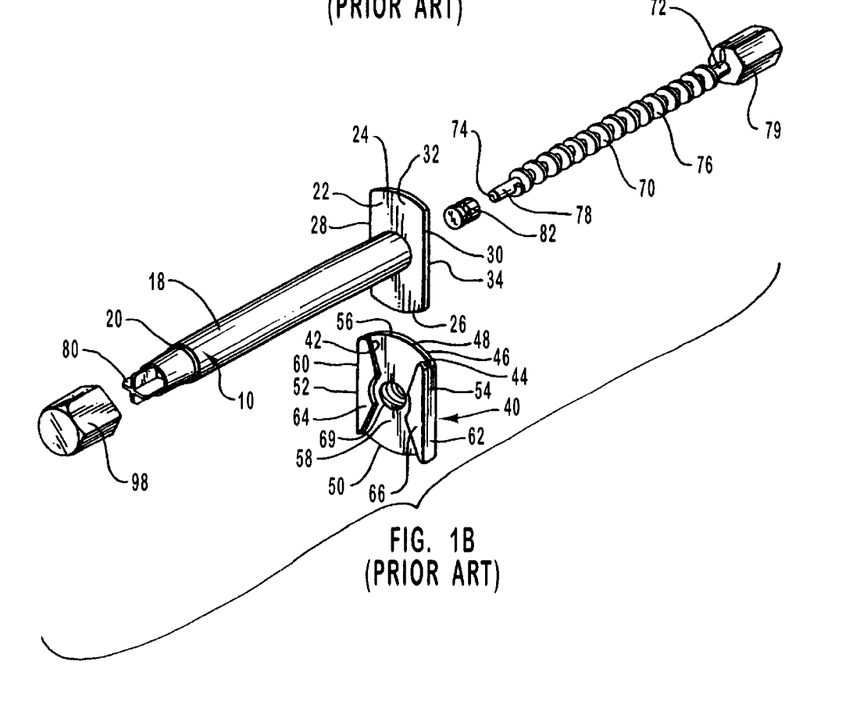
FIG. 1B is an exploded perspective view of the prior art device in FIG. 1A, having the cap removed from an end thereof.
Figure 1C:
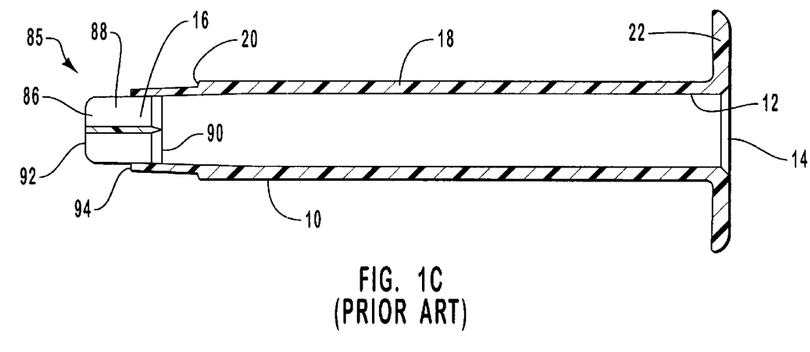
FIG. 1C is a cross-sectional view of the prior art device in FIG. 1A taken along the center longitudinal axis.

Various devices have thus been developed to facilitate the application of solid, yet pliable materials. An example of such a device is shown in FIGS. 1A, 1B, and 1C. FIG. 1A shows a syringe apparatus 100 the main elements of which are a barrel 10, a threaded plunger engager 40, a plunger 70, a plug 82, and a cap 98. Such a syringe is disclosed in detail in U.S. Pat. No. 5,618,273. U.S. Pat. No. 5,618,273 describes in detail the configuration of threaded plunger engager 40 and plunger 70 and how threaded plunger engager 40 facilitates operation of plunger 70.

As shown in FIGS. 1B and 1C, the barrel 10 terminates at its outlet end 16 with a delivery tip of the type disclosed in U.S. Pat. No. 5,387,103 and in U.S. Pat. No. 5,618,273. That is, barrel 10 further comprises a divider 80 for sectionalizing and individually compartmentalizing the composite material. Divider 80 has cutting plates 86 which are aligned on a longitudinal axis. Each cutting plate 86 has a leading beveled edge 90, which serves to cut the pliable material into individualized sections. This configuration enables each of the individualized sections of the material to be contained in a separate compartment. Each separate compartment accommodates the removal of a selected portion of the sectionalized and compartmentalized part of the material in the manner discussed in detail in U.S. Pat. No. 5,387,103; U.S. Pat. No. 5,603,701 and U.S. Pat. No. 5,618,273. Syringes having this design are presently sold by ULTRADENT PRODUCTS, INC. of South Jordan, Utah and the unique divider configuration is known as the QUADRASPENSE® delivery feature. Ultradent Products, Inc. sells a variety of dental compositions in syringes that utilize the QUADRASPENSE® delivery including VITALESCENCE® restorative material and AMELOGEN® restorative material.

Figure 1D:
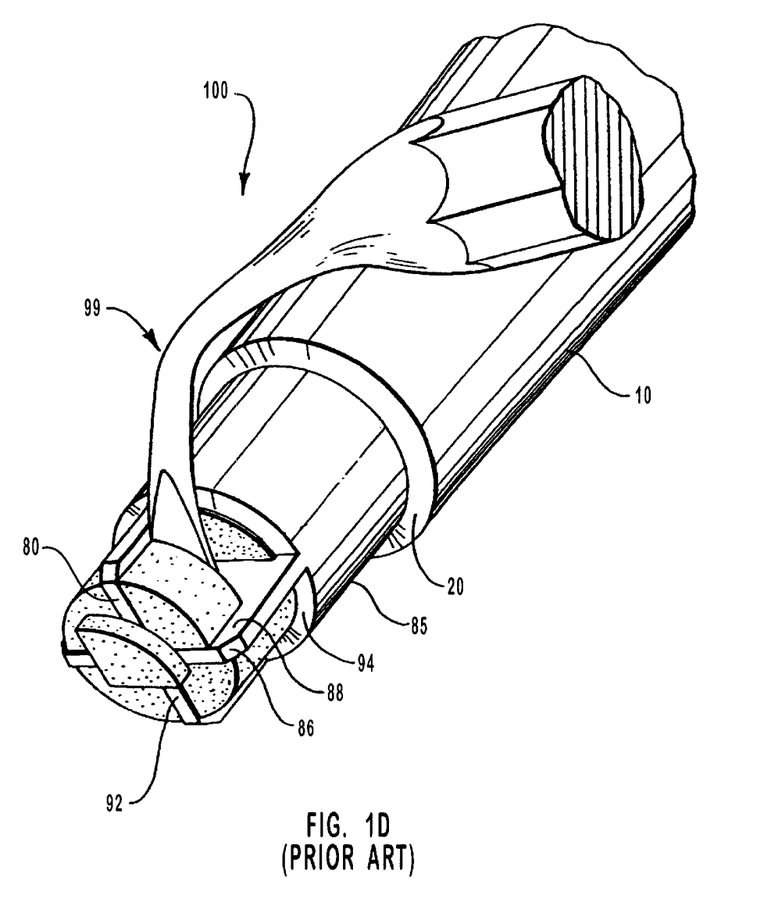
FIG. 1D is a perspective cutaway view of a shaping tool being used to pinch off a wedge of composite material from an end of the syringe apparatus of FIG. 1A.

Generally, as shown in FIG. 1D, an instrument 99 is used to sever or pinch off a piece of the sectionalized, compartmentalized pliable material. The instrument 99 is shown as being a spatula. The extruded portion of the material is shown as being separated and pinched off from the unextruded portion at outlet end 16 of barrel 10. Support surface 88 of cutting plate 86 serves as a cutting surface against which instrument 99 is contacted in order to sever the piece of composite material extending beyond the outlet end 16 of the barrel 10. The spatula easily removes a discreet amount and regular shape of the pliable material in such a way that the piece of material is easily manageable and controllable upon the end of instrument 99.

When used in conjunction with light-cured composite materials, the barrel, divider, and cap of the prior art apparatus discussed above is preferably made of a material which blocks transmission of the activating light so that the material remains pliable until ready to use. For example, a black-colored substance may be used to block transmission of activating light. While the foregoing syringe apparatus provides for an improved method of applying light-activated dental composites, there is a possibility that when the spatula 99 contacts the support surface 88 of cutting plate 86 (or any other surface of the barrel or divider), such contact may scratch or graze the surface, such that small pieces of black colored plastic material are removed. These small pieces may fall into the composite material, thereby causing discoloration of the composite material and, consequently, of the final dental construction. It would, therefore, be an advantage in the art to prevent discoloration of the dental composite material when such composite material is extracted from a delivery syringe to provide for more attractive dental constructions.

SUMMARY OF THE INVENTION

The present invention has been developed in response to the current state of the art, and in particular, in response to these and other problems and needs that have not been fully or adequately solved with regard to syringes used to apply light-activated dental composites. Thus, it is an overall object of embodiments of the present invention to provide for a syringe apparatus which prevents discoloration of dental composites through the inadvertent removal of dark plastic material into the dental composite material.

A feature of the present invention that enables these objects and advantages to be achieved is the use of different colored surfaces. One surface protects the dental composite material or other light-activating material from premature exposure to light while the other surface has a light color that is similar to that of the dental composite material. More particularly, this configuration typically involves the use of an opaque syringe barrel and a light colored outlet portion. The outlet portion may have many different configurations, however, one embodiment is sleeve shaped and extends coaxially within the barrel. The color of the outlet portion is compatible with that of the dental composite material or is at least more similar to the color of the dental composite material as compared with the opaque barrel. This combination allows a dental instrument such as a spatula to be used to scoop small quantities of the dental composite material from the outlet portion without concern that any piece of the light colored outlet portion inadvertently scraped off from the outlet portion is not visually detectable in the dental composite material. Note that it is typically necessary to use a spatula to remove the dental composite material since the material is relatively thick and viscous.

The outlet portion may extend beyond the barrel so that the outlet end of the outlet portion extends further than the outlet end of the barrel. The outlet portion may include a divider at its outlet end that divides the material into at least two separate compartmentalized portions. Many other embodiments are discussed below; however, each involves the use of two different colored surfaces to protect the material from being activated before the use of the material is desired and to ensure that dark plastic particles are not inadvertently deposited into the material when removing the material from the syringe.

Any suitable plunger may be utilized. A cap is used to cover the outlet end of the barrel and the outlet portion. The cap is opaque to prevent light from passing through the outlet portion and prematurely activating the dental composite material or other light-activating material.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The present invention is broadly described as a syringe apparatus for delivering light activated materials. Preferably, the present invention is used for delivering a light-activating dental composite material that cures when exposed to an activating light. Such light-activating dental composite material is well known in the art. A primary advantage of the present invention is the ability to protect the light-activated materials with an opaque material while ensuring that the light-activated material can be removed from the syringe apparatus without simultaneously dislodging small pieces of the opaque material. More particularly, the present invention eliminates the possibility of producing a tooth restoration with flecks of black plastic as a result of inadvertently scraping a black colored plastic material of a syringe that contains light-activated dental material when removing the dental material from the syringe. Since dental composite material is essentially solid yet pliable it is generally necessary to remove the material from a syringe with an instrument such as a spatula that may result in advertent scraping.

Figure 2A:
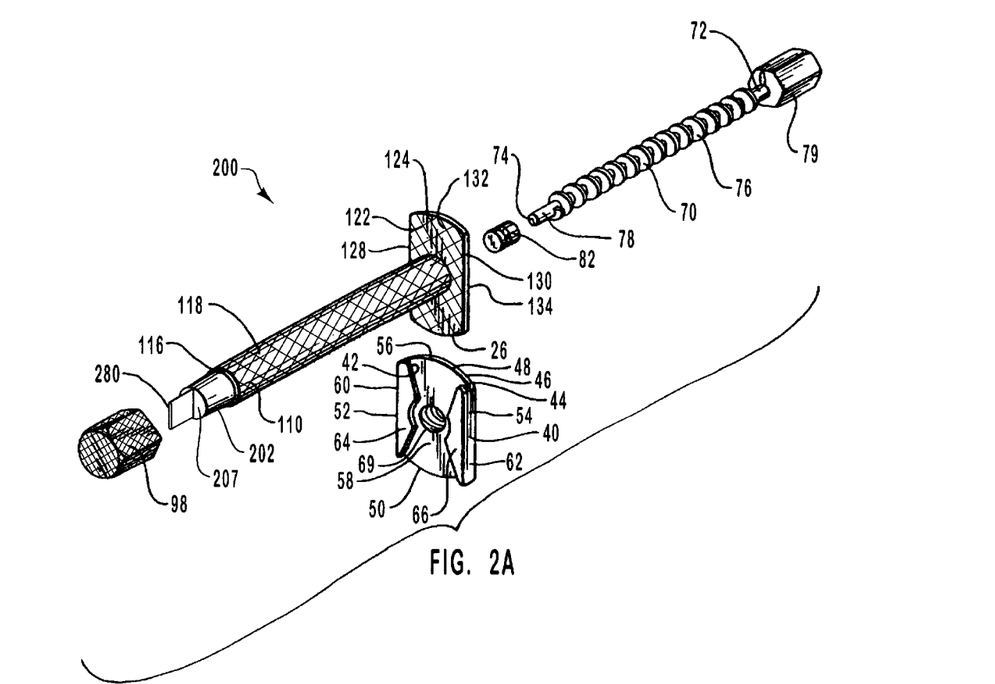
FIG. 2A is a perspective view of one presently preferred embodiment of the present invention.
Figure 2B:
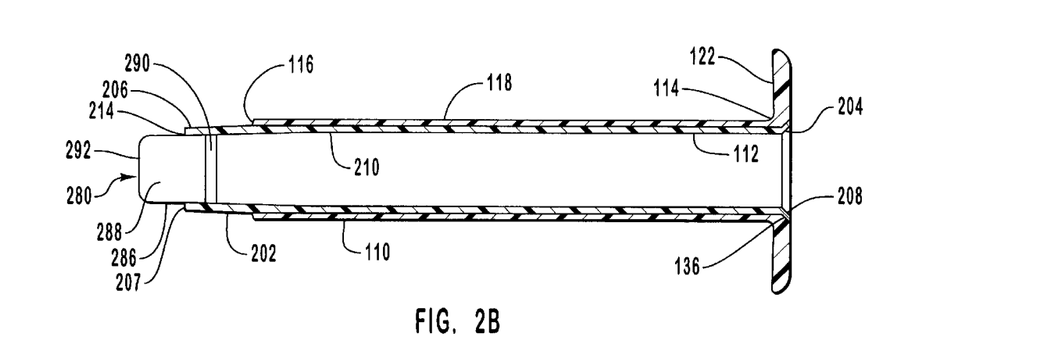
FIG. 2B is a cross-sectional view of the preferred embodiment of FIG. 2A taken along the center longitudinal axis.

An exemplary embodiment of the present invention is shown in FIGS. 2A–2B as the syringe apparatus generally designated at 200. Like syringe apparatus 100 shown in FIGS. 1A–1B, syringe apparatus 200 has a threaded plunger engager 40, a plunger 70, a plug 82, and a cap 98. These components of syringe apparatus 200 are essentially the same as those used with syringe apparatus 100 so they are numbered identically along with their various features. Although, threaded plunger engager 40, a plunger 70, a plug 82, and a cap 98 are shown with essentially the same configuration as is shown in FIGS 1A–1B, the drawings of the prior art, these components are described in detail below to provide a clear explanation of a preferred embodiment of the present invention.

Figure 2C:
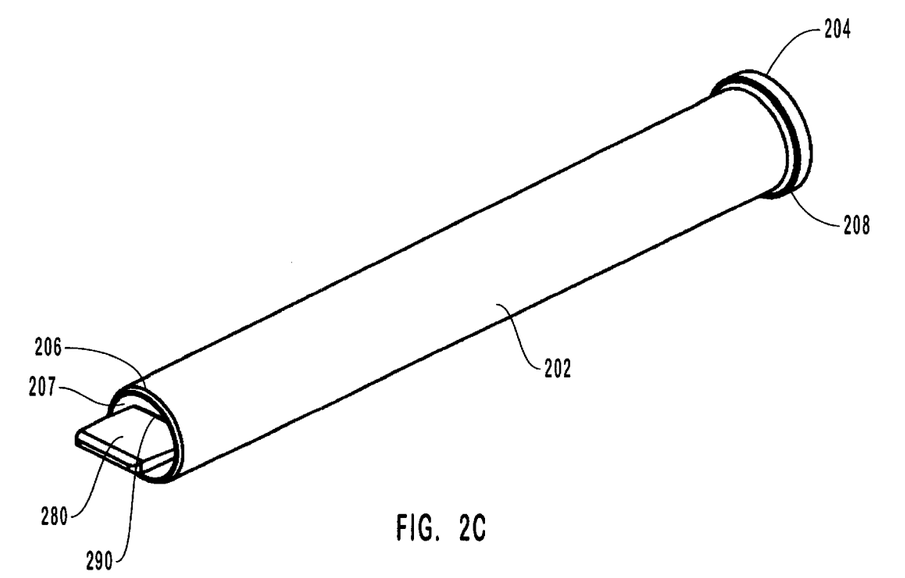
FIG. 2C is a perspective view of the preferred embodiment of the outlet portion having a divider.
Figure 3:
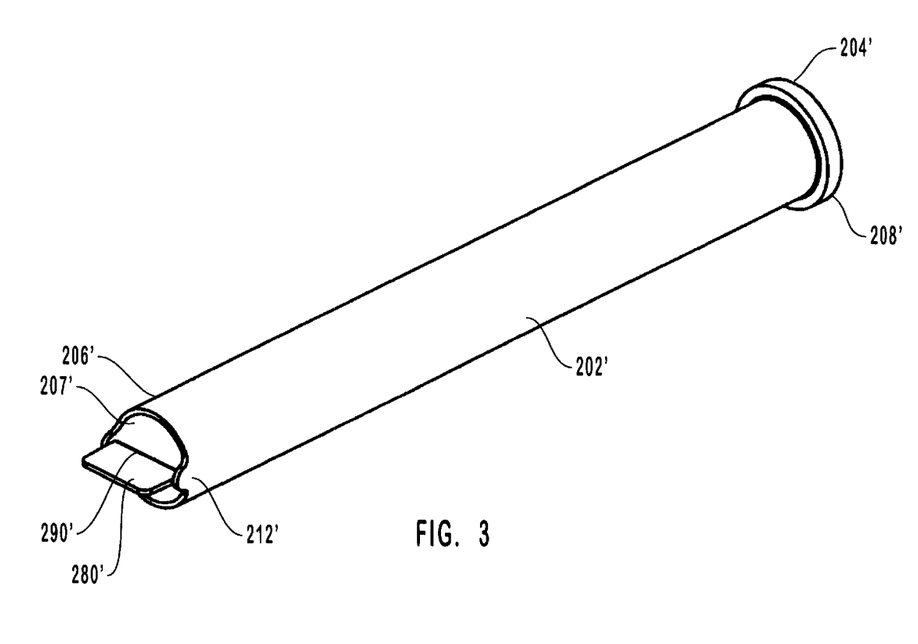
FIG. 3 is a perspective view of the preferred embodiment of the outlet portion, illustrating another embodiment having a divider.
Figure 4:
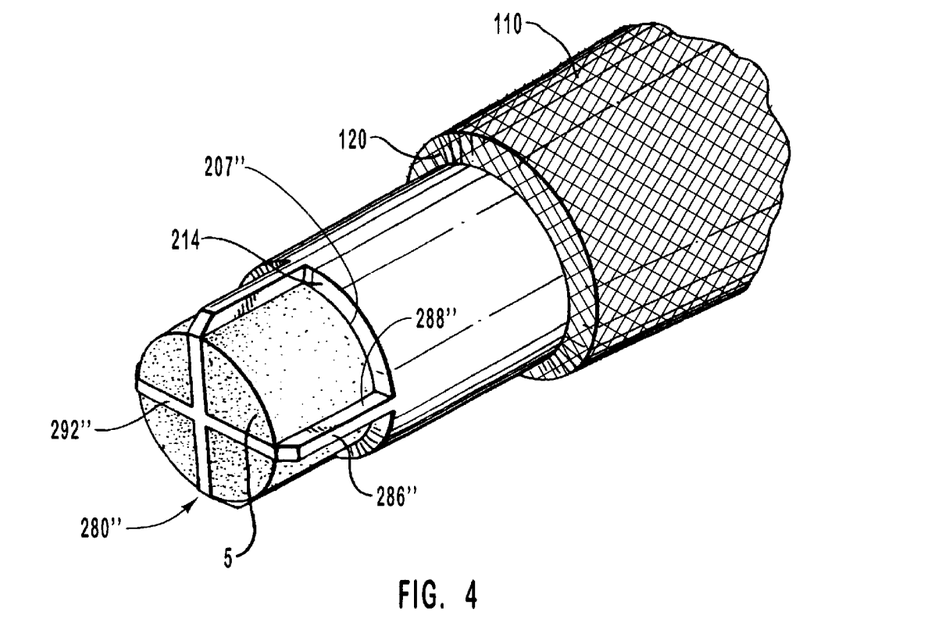
FIG. 4 is a detailed perspective view of an outlet end of the barrel and an outlet portion having a divider that is centered and configured to divide the light-activating material into four compartmentalized portions of equal volumes.
Figure 5:
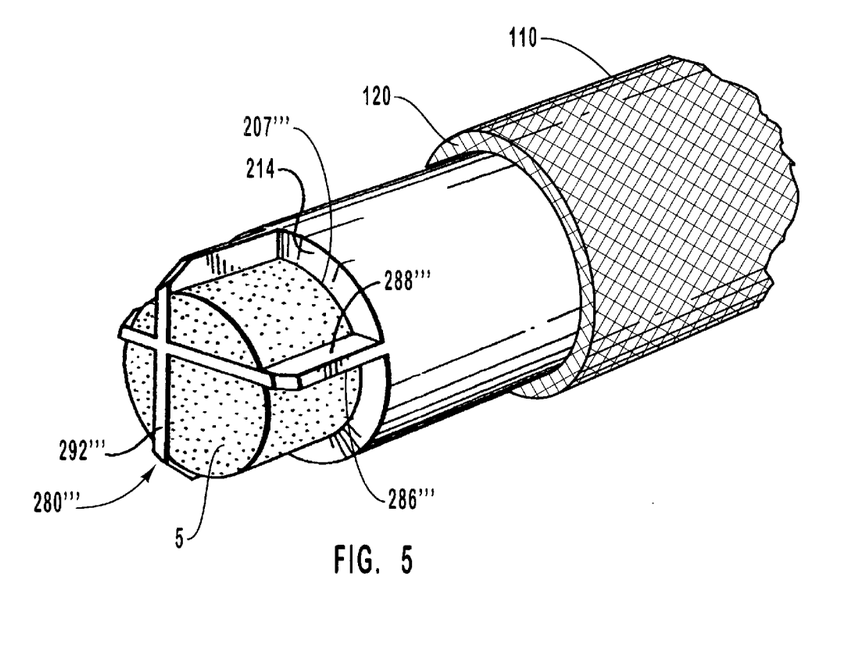
FIG. 5 is a perspective view similar to that shown in FIG. 5 depicting another embodiment of the present invention, illustrating variable-sized compartment sectionalizing through the use an offset divider configured to divide the light-activating material into four compartmentalized portions of unequal volumes.

The components of syringe apparatus 200 that are uniquely configured in the embodiment shown in FIGS. 2A–2B are the syringe barrel 110 and a tubular sleeve that serves as an outlet portion 202. To appreciate the advantages of outlet portion 202, syringe barrel 110 is briefly introduced below and then the other main components of syringe apparatus 200 are described in detail including plunger engager 40, plunger 70, plug 82, and cap 98. Once these elements are explained then outlet portion 202 is described in detail. FIG. 2C shows outlet portion 202 by itself and FIG. 3 provides an alternative embodiment of an outlet portion 202'. FIGS. 4–5 depict alternative designs of outlet portion 202 at 202' and 202'''. FIGS. 6–10 depict different embodiments of both the syringe barrel and the outlet portion.

Barrel 110 has a central bore 112, a proximal or inlet end 114, and a distal or outlet end 116. Barrel 110 terminates at its proximal or inlet end 114 in an integrally formed, enlarged finger grip 122, which is configured to accommodate the fingers of the user when the barrel is used with a standard, nonthreaded push-type plunger (not shown). Finger grip 122 is generally planar and is oriented perpendicular to the longitudinal axis of barrel 110. As best illustrated in FIG. 2A, finger grip 122 has rounded sides 124 and 126 located on two opposing sides, and two flat, parallel sides 128 and 130 located on the other two opposing sides. As further illustrated in FIG. 2A, the distance across finger grip 122 from flat side 128 to flat side 130 is less than the diameter measured across the rounded sides 124 and 126 of finger grip 122. Further, finger grip 122 provides a generally smooth, planar top surface 132 and a generally smooth, planar bottom surface 134.

As discussed in more detail below, threaded plunger engager 40 has slots or channels 42 and 44 configured to receive finger grip 122 of the barrel 110 in mating, press fit relationship. Threaded plunger engager 40 has a generally planar portion 46, the shape of which corresponds very closely to the shape of finger grip 122 described above. Planar portion 46 has rounded sides 48 and 50 located on two opposing sides, and two flat, parallel sides 52 and 54 located on the other two opposing sides. Planar portion 46 provides a generally smooth, planar top surface 56 and a generally smooth, planar bottom surface 58. Integrally formed at the outer edges of flat sides 52 and 54 are two side wall portions 60 and 62, which are oriented perpendicular to planar portion 46. Integrally formed at the distal ends of side wall portions 60 and 62 are flanges 64 and 66, which are oriented perpendicular to, and extend inwardly from, side wall portions 60 and 62. Bottom surface 58, side wall portions 60 and 62, and flanges 64 and 66 cooperate to form slots or channels 42 and 44 for receiving the flat sides 128 and 130 of finger grip 122 in sliding, press fit engagement. As further shown in FIG. 2A, flanges 64 and 66 are slightly chamfered so as to guide finger grip 122 into engagement with threaded plunger engager 40. In addition, the lateral separation between the distal ends of flanges 64 and 66 is slightly less than the outside diameter of barrel 110 adjacent to finger grip 122, so as to provide secure engagement between finger grip 122 and threaded plunger engager 40 when finger grip 122 is fully inserted into threaded plunger engager 40. Threaded plunger engager 40 further comprises a throughbore 69, with internal threading. The throughbore 69 passes through the center of planar portion 46 of threaded plunger engager 40.

Plunger 70 has a proximal end 72, a distal end 74, a threaded stem 76, an unthreaded distal tip 78, and an integrally formed, hexagonally shaped head 79. The external threads of threaded stem 76 are complementary of, and configured to mate with, the internal threads of the throughbore 69 of the threaded plunger engager 40. The outside diameter of the threads of threaded stem 76 is approximately the same, yet is slightly smaller than, the internal diameter of central bore 112 of barrel 110, such that threaded stem 76 will slide with close tolerance within central bore 112. Distal end 74 engages plug 82 in a manner such that plug 82 is urged against a material contained within the barrel 110, such as material 5 of FIG. 5, and provides a seal to prevent the material from flowing around plug 82.

The present invention contemplates this preferred design of threaded plunger engager 40 and plunger 70 because of features provided by this design as discussed in U.S. Pat. No. 5,618,273, herein incorporated by reference. More particularly, such a design is particularly useful with the delivery of material that is highly viscous or essentially solid, yet pliable. However, one skilled in the art will recognize that any plunger design may be used without departing from the scope of the present invention. Some examples of other plunger configurations are disclosed in several patents owned by ULTRADENT PRODUCTS, INC. including: U.S. Pat. No. 4,986,820; Design U.S. Pat. No. 322,317 and in U.S. Pat. No. 5,665,066. These patents are hereby incorporated by reference.

In practice, barrel 110 stores or contains the light-activating dental composite until it is ready to be used. Because syringe apparatus 200 is used to deliver a light-activating material such as a dental composite material, barrel 110 and cap 98 are constructed of or coated by a substance having a component that blocks transmission of the activating light which causes the light-activating material therein to begin curing. Preferably, such a light-blocking substance will be opaque such that the passage of light or other activating radiant energy is blocked. For example, barrel 110 may be constructed of a black material or coated with a black material.

Cap 98 is installed at the outlet end 206 of the outlet portion 202 so that it can be selectively removable from, and placed over, the individualized sections of the pliable material 5 which have been presented beyond the outlet end 206 of the outlet portion 202. Preferably, cap 98 should fit tightly at its proximal end against the outlet end 116 of barrel 110. The tight fit between the proximal end of cap 98 and the outlet end 116 of barrel 110 is to ensure that the composite material within the barrel 110 is not exposed to ambient conditions. Cap 98 also features a recessed internal surface (not shown) that overlays and covers the segment of the material divider 280 that extends beyond the outlet end 206 of outlet portion 202. FIG. 2A shows cap 98 removed from the outlet end 206 of the outlet portion 202. Thus, opaque cap 98 may be selectively removed so that the light-activating material can be delivered from the syringe and be remounted over the outlet end to block the transmission of light that may activate the material.

As shown in FIG. 2A, outlet portion 202 is provided to deliver the dental composite material as it is expressed from the barrel 110. Outlet portion 202 has an inlet end 204 opposite from outlet end 206. Outlet portion 202 is tubular and extends coaxially within barrel 110. As shown, outlet portion 202 preferably extends coaxially within barrel 110 throughout the entire length of barrel 110. Also, outlet portion 202 preferably extends beyond outlet end 116 of barrel 110, as shown in FIGS. 2A and 2B. Inlet end 204 of outlet portion 202 is essentially coterminus with inlet end 114 of barrel 110 as shown in FIG. 2B. This enables threaded plunger engager 40 to be positioned on finger grip 122 of the barrel 110 without modification.

Outlet portion 202 may be attached to barrel 110 by any means known in the art such as, but not limited to, press fitting, adhesive bonding, and the like. Those skilled in the art will recognize that outlet portion 202 may be integrally formed with barrel 110 by means such as injection molding, two-color molding, chemical adhesion, and the like.

In a preferred embodiment, as shown in FIG. 2B, inlet end 204 of outlet portion 202 is shown to have a flange 208 that flares radially outward. Inlet end 114 of barrel 110 is configured with a corresponding shoulder 136 formed parametrically around the circumference of bore 112 at inlet end 114. Flange 208 and shoulder 136 are configured to facilitate a press-fit engagement of barrel 110 and outlet portion 202. One will recognize that other configurations exist for press-fitting barrel 110 and outlet portion 202. For example, outlet portion 202' in FIG. 3 has a flange 208' that extends perpendicularly and radially outward at inlet end 204'.

Preferably, outlet end 206 of outlet portion 202 has an outlet orifice 207 through which dental composite material exits barrel 110 as it is expressed from the barrel. The outlet portion 202 may terminate in various configurations. However, the outlet portion 202 preferably has a material supporter at its outlet end that is configured to support the light-activating material as it is removed by a dental instrument. A preferred embodiment of such a material supporter is a material divider 280 that also divides the material. In the embodiment shown in FIGS. 2A–2C, material divider 280 is a portion integrally attached to outlet portion 202 at outlet end 206 for sectionalizing and individually compartmentalizing the material as it is extruded. One skilled in the art will also recognize that material divider 280 may also be non-integrally attached to outlet portion 202.

The net result of the action between the outlet portion 202 and its associated divider 280 with plunger 70 is that the material 5 will be presented beyond the outlet end 206 of the outlet portion 202 in two individualized sections. The use of a divider to sectionalize and individually compartmentalize material 5 as the plunger 70 pushes the material 5 to the outlet end 206 of the outlet portion 202 is particularly advantageous in dentistry. The divider enables the dental practitioner to use the divider as a palette and to remove small portions of material 5 in the amount that is needed to incrementally complete the dental restoration.

Divider 280 is essentially a single cutting plate 286 having opposing support surfaces 288. Cutting plate 286 is centered within outlet portion 202 at its outlet end 206. Cutting plate 286 has a leading beveled edge 290, which serves to cut the pliable material 5 into individualized sections as it is extruded from barrel 110. Cutting plate 286 also has an opposite trailing edge 292 that extends beyond the outlet end 206 of outlet portion 202.

Each separate compartment of divider 280 has a support surface 288 that extends beyond the outlet end 206 of the outlet portion 202. Each section of material lies within a compartment formed by the inside surface 210 of outlet portion 202, and at least one support surface 288 of cutting plate 286. Each separate compartment accommodates the removal of a selected portion of the sectionalized and compartmentalized part of the material 5 in the manner discussed in detail in U.S. Pat. No. 5,327,103.

In the embodiment shown in FIGS 2A–2B, leading beveled edge 290 of cutting plate 286 is situated fully within outlet portion 202. In the embodiment shown in FIG. 3, beveled edge 290' is attached to outlet end 206' of outlet portion 202' at extensions 212' such that material 5 exits outlet orifice 207' as it encounters leading beveled edge 290'. An advantage of this configuration is that there is no increase in pressure required to expel material 5 since divider 280' divides material 5 as material 5 exits outlet orifice 207'.

In a presently preferred embodiment, cutting plate 286 is centered relative to the center of barrel 110, providing equal volumes of sectionalized material. One skilled in the art will recognize that cutting plate 286 may also be offset if unequal volumes of sectionalized material are desired.

A material divider may be configured in various ways. For example, material divider 280 may comprise a divider such as material divider 280 as shown in FIGS. 2A–2C or material divider 280' as shown in FIG. 3. Alternatively, the divider may be configured to divide the material into more than two separate portions such as the dividers shown in FIGS. 4–5 and like the dividers disclosed in U.S. Pat. No. 5,387,103 and in U.S. Pat. No. 5,618,273.

As illustrated in FIGS. 4–5, an outlet portion may alternatively have a divider for sectionalizing and individually compartmentalizing the material 5 into more than two separate portions. More particularly, an outlet portion is illustrated in FIGS. 4–5 respectively at 202" and 202'" that have respective dividers 280" and 280'" configured to divide the material into four separate portions. Each of the dividers 202" and 202'" has cutting plates that are identified respectively at 286" and 286'". Each of the cutting plates has opposing support surfaces identified in FIGS. 4–5 respectively at 288" and 288'". Each cutting plate has a leading beveled edge for cuffing the pliable material 5 into individualized sections. Like the embodiment shown in FIGS. 2A–2C, the leading beveled edge of each cutting plate preferably lies within the outlet portion. The cutting plates also include opposite trailing edges identified at 292" and 292'". Each section of material lies within a compartment formed by the inside surface of the outlet portions 202" and 202'" and adjacent support surfaces 288" and 288'" of the adjacent cutting plates 286" and 286'".

In a presently preferred embodiment, each of the cuffing plates 286" and 286'" radially extend from a single longitudinal axis. The longitudinal axis from which the cutting plates 286" and 286'" radiate may be centered relative to the center of the barrel 110 as shown in FIG. 4, or may be offset if unequal volumes of sectionalized material are desired as shown in FIG. 5. Providing separate compartments of unequal volumes to obtain corresponding individualized sections of the material 5 as shown in FIG. 5 is useful when varying amounts of the material are required.

Figure 6:
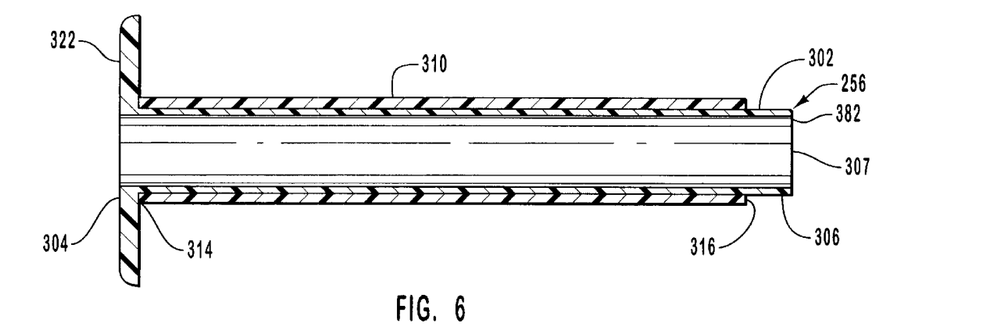
FIG. 6 is a cross-sectional view of yet another embodiment of the present invention taken along the center longitudinal axis, illustrating the invention with an opaque sleeve around a barrel that has a color that is more similar to the color of the light-activating material contained in the barrel than it is to the opaque sleeve.
Figure 7:
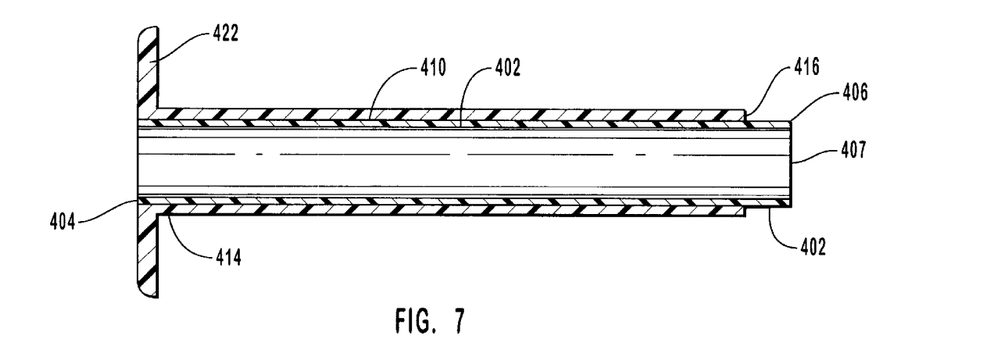
FIG. 7 is a cross-sectional view of yet another embodiment of the present invention taken along the center longitudinal axis, illustrating the invention with the outlet portion having an outlet orifice that has no divider or flanged retaining lip.
Figure 8:
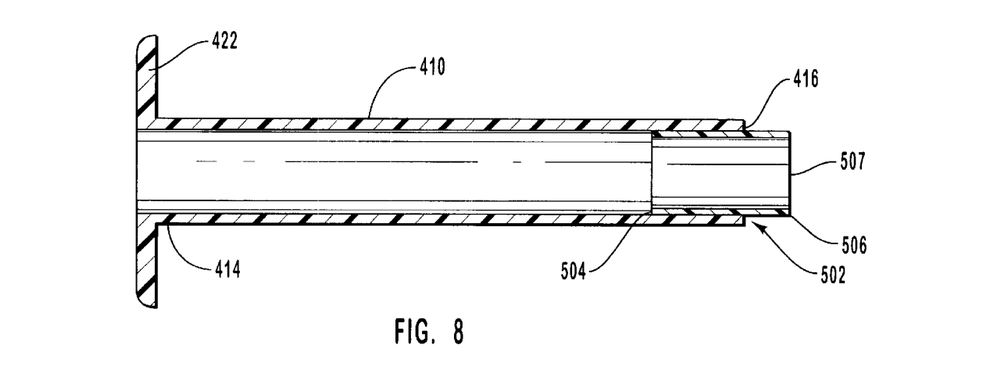
FIG. 8 is a cross-sectional view of yet another embodiment of the present invention taken along the center longitudinal axis, illustrating the invention with the outlet portion having an outlet orifice that has no divider or flanged retaining lip.

FIG. 6 depicts another embodiment in which the tubular sleeve 310 is mounted over the syringe barrel, which thus provides the outlet portion 302. Like the embodiments described above that have a material supporter such as material divider 280, outlet portion 302 also has a material supporter. The material supporter of outlet portion 302 is a retaining lip 382 that is disposed at outlet end 306 of outlet portion 302. Retaining lip 382 serves to support the material 5 as it is extruded through barrel 310. Retaining lip 382 extends parametrically and radially inward around outlet end 306 of outlet portion 302.

In FIG. 6 the outlet portion 302 extends only partially within sleeve 310 so that inlet end 304 is not coterminous with inlet end 314 of sleeve 310. Since only a small segment of each outlet portion is contacted by instruments used to remove material, an embodiment as shown in FIG. 6 provides a cost benefit without altering the effectiveness of the design. More particularly, a short outlet portion such as outlet portion 302 requires less material than the other designs and yet the instrument is prevented from scraping an opaque material from sleeve 310. Such an outlet portion may be held in place within the barrel through a press-fit configuration or through complementary features that act together to anchor the outlet portion in the barrel.

Figure 9:
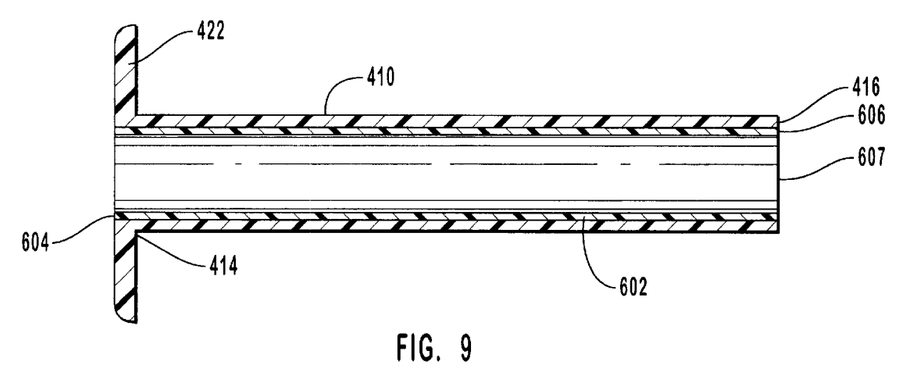
FIG. 9 is a cross-sectional view of yet another embodiment of the present invention taken along the center longitudinal axis, illustrating the invention with an outlet portion having an outlet orifice that has no divider or flanged retaining lip.

FIG. 9 depicts an embodiment that is similar to the embodiment depicted in FIGS. 2A–2C, however, the outlet portion 602 terminates such that there is merely an outlet orifice 607 without any other features. More particularly, outlet portion 602 has no material supporter such as a material divider or a retaining lip. The outlet portion may have any suitable terminal configuration. For example, the outlet end 606 of the outlet portion 602 may be a luer fitting or other type of fitting commonly used at the distal end of dental or medical syringes through which the dental composite material is extruded. Note that inlet end 604 of outlet portion 604 is not flared. Inlet end 414 of barrel 410 is correspondingly straight so that the barrel 410 and the outlet portion 602 have parallel sidewalls along their entire lengths. The sidewalls may also be nonparallel to enhance the ability to obtain a press-fit engagement of barrel 410 and outlet portion 602.

As indicated above, the outlet end of each outlet portion may have any suitable configuration. For example, the outlet end may be coterminus with the outlet end 416 of the barrel such as outlet end 606 of outlet portion 602 shown in FIG. 9. It is preferred, however, to have some of the outlet portion extend beyond the barrel as in the other embodiments so that it is easier for an instrument to remove the material.

Figure 10:
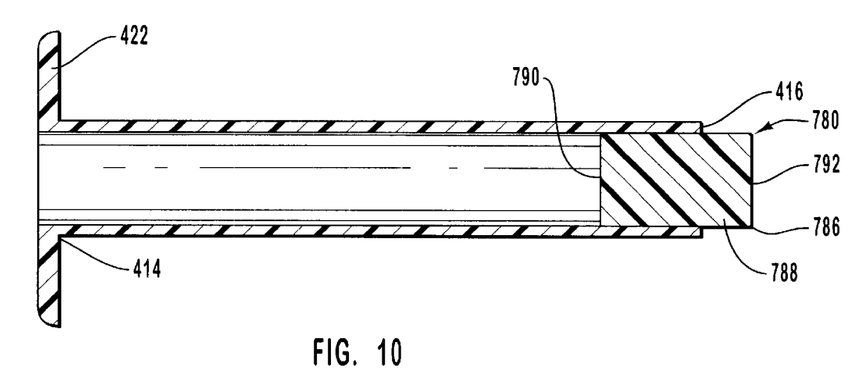
FIG. 10 is a cross-sectional view of yet another embodiment of the present invention taken along the center longitudinal axis, illustrating the invention with an outlet portion that includes a divider attached to the outlet end of the barrel.

In yet another embodiment shown in FIG. 10, the outlet portion may be merely a divider 780 attached to the outlet end 416 of the barrel for sectionalizing and individually compartmentalizing the material as it is extruded. One skilled in the art will recognize that although material divider 780 may be integrally or nonintegrally attached to outlet end 416 of the barrel. Like divider 280, divider 780 is essentially a single cutting plate 786 having opposing support surfaces 788. Cutting plate 786 is centered within the barrel at its outlet end 416. Cutting plate 786 has a leading beveled edge 790, which serves to cut the pliable material into individualized sections as it is extruded from the barrel. Cutting plate 786 also has an opposite trailing edge 792 that extends beyond the outlet end 416 of the barrel. Note that the outlet portion may similarly be merely a retaining lip having the appropriate color compatibility with the material in the barrel.

Note that divider 780 is shown in FIG. 10 with different cross-hatching from the barrel to indicate that different materials are used to form these two components. However, these components may be formed from the same material and merely have an appropriate coating.

Preferably, the outlet portion and the optional material supporters such as a material divider or a retention lip are constructed of or coated by a substance that is more similar to the color of the dental composite material as compared to the light-blocking substance of the barrel. At least one surface of the outlet portion has a color that similar to the composite material. Hence, the syringe apparatus essentially has a tubular barrel with a light-blocking portion (e.g., the black-colored barrel) and an outlet portion (e.g., the composite-colored tubular outlet portion). The composite-colored configuration is advantageous for the purpose of providing aesthetic dental constructions. As the dentist is removing the dental composite material 5 from the outlet portion, inadvertent scraping of pieces or flakes of the outlet portion does not result in the addition of these pieces to the dental composite material in a manner that is noticeable by the naked eye. That is, a person will not be able to visually detect any discoloration in the final dental construction. Thus, the present invention provides for the barrel and the outlet portion to have different color characteristics to address the need in the art for more aesthetic dental constructions.

The barrels described hereinabove such as barrels 110, 310 and 410 are all examples of barrel means for containing light-activating materials such as a dental composite material. The barrel means has light-blocking means for blocking transmission of activating light to the dental composite material contained within the barrel means. Examples of light-blocking means include the pigmentation in the barrel means such that the barrel means is opaque or an opaque coating on the barrel means.

Preferably, the outlet portion and the optional material supporters such as a material divider or a retention lip are constructed of or coated by a substance that is more similar to the color of the dental composite material as compared to the light-blocking substance of the barrel. At least one surface of the outlet portion has a color that similar to the composite material. Hence, the syringe apparatus essentially has a tubular barrel with a light-blocking portion (e.g., the black-colored barrel) and an outlet portion (e.g., the composite-colored tubular outlet portion). The composite-colored configuration is advantageous for the purpose of providing aesthetic dental constructions. As the dentist is removing the dental composite material from the outlet portion, inadvertent scraping of pieces or flakes of the outlet portion does not result in the addition of these pieces to the dental composite material in a manner that is noticeable by the naked eye. That is, a person will not be able to visually detect any discoloration in the final dental construction. Thus, the present invention provides for the barrel and the outlet portion to have different color characteristics to address the need in the art for more aesthetic dental constructions.

Material dividers such as dividers 280, 280', 280", 280''' and 780 are all examples of means for dividing the light-activating material into at least two separate portions as the material is pushed beyond the outlet end of the barrel means. Retaining lip 382 is an example of means for defining an outlet orifice and for retaining the light-activating material at the outlet orifice. The material dividers and the retaining lips are also all examples of means for supporting the light-activating material so that the material is retained in a manner that enables small portions of the material to be removed by an instrument such as a dental instrument.

The plungers disclosed herein such as plunger 70 are examples of plunger means for effecting delivery of the light-activating material out of the outlet means of the barrel means as the plunger means is pushed through the barrel means towards the outlet end of the barrel means against the material.

In summary, the dental syringe system of the present invention enables the efficient storage and dispensing of solid, yet pliable materials, such as dental composites with a minimum of wasted material. The present invention also provides a syringe apparatus comprising a syringe barrel that can be utilized with either a standard push-type plunger or be retrofitted for use with a threaded, rotation-type plunger. The dental syringe system also provides discrete and separated doses (or wedges) of a solid but pliable extrudent as the material is extruded from the syringe system. The doses are easily pinched off by a shaping tool against the support surfaces that extend beyond the outlet end of the barrel. The barrel and cap block transmissive exposure of the material therein to an activating light so as to prevent premature curing of the light activated material therein. Most importantly, the distinctive coloring of the outlet portion and the delivery means provides for more aesthetic dental constructions.

FIG. 6 depicts an additional embodiment of the present invention. The embodiment shown in FIG. 10 depicts an opaque tubular sleeve 310 having an inlet end 314 and an outlet end 316. A barrel adapted to contain a light-activating material is shown at 302 having an inlet end 304 and an outlet end 306. Barrel 302 extends coaxially within opaque tubular sleeve 310. Barrel 302 has a light color that is more similar to the color of the light-activating material as compared with opaque tubular sleeve 310 such that any piece of the barrel inadvertently scraped off by an instrument used to scoop small quantities of the light-activating material from the barrel is not visually detectable in the light-activating material.

Note that although barrel 302 and sleeve 310 are separate components, they may also be integral. Sleeve 310 is formed of or coated with an opaque substance to protect the dental composite material or other light-activating material contained therein. In this present embodiment, sleeve 310 may also represent a coat of an opaque substance covering outlet portion 302, such that the light-activating material is protected from radiant light.

Outlet end 306 of barrel 302 extends beyond outlet end 316 of sleeve 310. Outlet end 306 of barrel 302 defines an outlet orifice 307 through which material exits barrel 302 as it is expressed from barrel 302. Outlet end 306 may be configured as shown or with any suitable light-activating material supporter at the outlet orifice such as the supporters described above that are configured to retain the light-activating material in a manner that enables small quantities of the light-activating material to be removed by an instrument.

Barrel 302 terminates at its inlet end 304 in an integrally formed, enlarged finger grip 322. This finger grip 322 can also engage threaded plunger engagers like those discussed above in reference to engager 40. More particularly, since inlet end 304 of barrel 302 and inlet end 314 of sleeve 310 are essentially coterminus a threaded plunger engager may be positioned on finger grip 322 of the barrel 302 without modification.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dental syringe apparatus used in delivering a light-activating dental composite material which cures when exposed to an activating light, comprising:

a tubular sleeve having an inlet end and an outlet end;

a barrel having an inlet end and an outlet end;

said tubular sleeve and barrel being cylindrically arranged in relation to one another so that one of them is cylindrically mounted within the other, and wherein whichever one of said tubular sleeve and barrel is mounted on the inside serves as an outlet portion that contains a light activating material, said outlet portion comprising a material that is sufficiently similar in color to the light activating material as to be essentially unnoticeable in comparison to the light activating material, and whichever of said tubular sleeve and barrel is mounted on the outside serves as a light-blocking portion and is comprised of an opaque material that prevents activating light from reaching the light activating material; and a plunger adapted for slidable movement within whichever of said tubular sleeve and barrel is mounted on the inside of the other, in order to effect delivery of the light activating material as the plunger is advanced from the inlet toward to the outlet end thereof.

2. A syringe apparatus as defined in claim 1, wherein the barrel and the outlet portion are separate components.

3. A syringe apparatus as defined in claim 1, wherein the barrel and the outlet portion are integral.

4. A syringe apparatus as defined in claim 1, wherein the outlet portion extends coaxially within the barrel.

5. A syringe apparatus as defined in claim 1, wherein the outlet portion extends coaxially within the barrel along at least most of the length from the inlet end of the barrel to the outlet end of the barrel.

6. A syringe apparatus as defined in claim 1, wherein the outlet portion extends coaxially within the barrel and wherein the outlet portion extends beyond the barrel at the outlet end of the barrel.

7. A syringe apparatus as defined in claim 1, wherein the outlet portion extends coaxially within the light-blocking portion and wherein the outlet portion and the light-blocking portion are coterminous at the outlet end of the barrel.

8. A syringe apparatus as defined in claim 1, wherein the outlet portion has at least one dental composite material supporter configured to retain the dental composite material in a manner such that small portions of the dental composite material can be removed by a dental instrument.

9. A syringe apparatus as defined in claim 8, wherein the outlet portion extends coaxially within the barrel.

10. A syringe apparatus as defined in claim 8, wherein the outlet portion extends beyond the outlet end of the barrel.

11. A syringe apparatus as defined in claim 8, wherein the at least one dental composite material supporter is at least one dental composite material divider at said outlet end of said barrel that is configured to divide the dental composite material into at least two separate portions as the dental composite material is pushed beyond said outlet end of said barrel.

* * * * *

UNITED STATES PATENT AND TRADEMARK OFFICE
CERTIFICATE OF CORRECTION

PATENT NO. : 6,569,122 B2
DATED : May 27, 2003
INVENTOR(S) : Dan E. Fischer, Richard N. Rachal and Bruce S. McLean It is certified that error appears in the above-identified patent and that said Letters Patent is hereby corrected as shown below:

Column 3,
Line 63, after "use" insert -- of --

Column 5,
Line 15, change "202'" to -- 202' ' --

Column 6,
Line 66, change "coterminus" to -- coterminous --

Column 9,
Line 26, change "coterminus" to -- coterminous --
Line 59, after "that" insert -- is --
Line 66, delete "5"

Column 10,
Lines 18-39, replace this paragraph with the following, original paragraph:

--The various outlet portions described above are all examples of outlet means for enabling the light-activating material to exit the barrel means as it is expressed from the barrel means and for permitting the material to be exposed such that an instrument such as a dental instrument can be used to scoop small quantities of the material from the outlet means. The outlet means is located at the outlet end of the barrel means, however, the outlet means may extend the entire length of the barrel means. The outlet means has at least one surface with a light color that is more similar to the color of the dental composite material or other light-activating material as compared with the light-blocking means such that any piece of the light colored surface of the outlet means inadvertently scraped off by a dental instrument used to scoop small quantities of the dental composite material from the outlet means is not visually detectable in the dental composite material.--

UNITED STATES PATENT AND TRADEMARK OFFICE
CERTIFICATE OF CORRECTION

PATENT NO. : 6,569,122 B2
DATED : May 27, 2003
INVENTOR(S) : Dan E. Fischer, Richard N. Rachal and Bruce S. McLean It is certified that error appears in the above-identified patent and that said Letters Patent is hereby corrected as shown below:

<u>Column 11,</u>
Line 10, change "10" to -- 6 --
Line 46, change "coterminus" to -- coterminous --

Signed and Sealed this

Eighteenth Day of November, 2003

JAMES E. ROGAN
*Director of the United States Patent and Trademark Office*